United States Patent [19]
Sickora et al.

[11] Patent Number: 6,077,501
[45] Date of Patent: Jun. 20, 2000

[54] DENTURE CLEANSER

[75] Inventors: Vincent J. Sickora, Convent Station; Paul X. Riccobono, Bedminster, both of N.J.

[73] Assignee: Block Drug Company, Inc., Jersey City, N.J.

[21] Appl. No.: 09/107,312

[22] Filed: Jun. 30, 1998

[51] Int. Cl.[7] .............. A61K 7/16; C11D 7/54; C11D 3/395; C11D 1/02

[52] U.S. Cl. .............. 424/49; 510/100; 510/117; 134/2; 134/42; 424/401; 424/466

[58] Field of Search .............. 424/49–88; 510/100, 510/117

[56] References Cited

U.S. PATENT DOCUMENTS

| | | | |
|---|---|---|---|
| Re. 32,771 | 10/1988 | Eoga | 252/99 |
| 3,483,033 | 12/1969 | Casey | 127/61 |
| 3,577,490 | 5/1971 | Welsh et al. | 264/120 |
| 3,751,372 | 8/1973 | Zecher | 252/81 |
| 3,793,211 | 2/1974 | Kohlhepp et al. | 252/99 |
| 3,821,117 | 6/1974 | Breece et al. | 252/99 |
| 3,962,107 | 6/1976 | Levin et al. | 252/100 |
| 4,169,817 | 10/1979 | Weber | 252/545 |
| 4,217,234 | 8/1980 | Krisp et al. | 252/99 |
| 4,256,599 | 3/1981 | Krisp et al. | 252/99 |
| 4,344,932 | 8/1982 | Gordon | 132/73 |
| 4,357,318 | 11/1982 | Sihah et al. | 424/52 |
| 4,395,346 | 7/1983 | Kleist | 252/135 |
| 4,486,330 | 12/1984 | Yoshida et al. | 252/174 |
| 4,701,223 | 10/1987 | Eoga | 134/2 |
| 4,747,880 | 5/1988 | Berrido et al. | 252/135 |
| 4,762,638 | 8/1988 | Dollman et al. | 252/135 |
| 4,851,146 | 7/1989 | Hosoi et al. | 252/102 |
| 5,015,408 | 5/1991 | Reuss | 252/99 |
| 5,055,305 | 10/1991 | Young | 424/466 |
| 5,120,460 | 6/1992 | Asai et al. | 252/106 |
| 5,147,632 | 9/1992 | Pan et al. | 424/54 |
| 5,384,062 | 1/1995 | Eoga et al. | 252/99 |
| 5,437,856 | 8/1995 | Lukacovic et al. | 424/50 |
| 5,460,802 | 10/1995 | Asami et al. | 424/49 |
| 5,476,607 | 12/1995 | Eoga et al. | 252/99 |
| 5,482,646 | 1/1996 | Mazzola | 252/174 |
| 5,486,304 | 1/1996 | Eoga et al. | 252/99 |
| 5,529,788 | 6/1996 | DeSenna | 424/466 |
| 5,571,519 | 11/1996 | Synodis et al. | 242/405 |

FOREIGN PATENT DOCUMENTS

| | | |
|---|---|---|
| 941705 | 2/1974 | Canada. |
| 466244 | 1/1992 | European Pat. Off.. |
| 1 545 299 | 11/1967 | France. |
| 1 374 105 | 11/1974 | United Kingdom. |
| 1 579 401 | 11/1980 | United Kingdom. |
| WO/PCT87/01562 | 3/1987 | WIPO. |
| WO/PCT94/18301 | 8/1994 | WIPO. |
| WO/PCT99/07818 | 2/1999 | WIPO. |

*Primary Examiner*—Shep K. Rose

[57] ABSTRACT

A denture cleanser tablet or other cleaning composition comprises a synergistic combination of a hexametaphosphate, such as sodium hexametaphosphate, and an ethylenediamine tetraacetic acid (Versene Acid or EDTA) or a salt thereof. The cleaning composition can be prepared without peracids or peracid salts, which leads to a milder, but highly effective, cleaning composition.

14 Claims, No Drawings

DENTURE CLEANSER

BACKGROUND OF THE INVENTION

1. Field of the Invention

The invention relates to a denture cleanser tablet composition and to methods of making and using a denture cleanser tablet composition.

2. Description of Related Art

Full or partial dentures are intended to be worn in the mouth to replace missing teeth. Like teeth, dentures should be cleaned regularly to maintain good oral health. Like teeth, dentures should also be cleaned regularly for cosmetic reasons.

Unlike teeth, dentures can be removed for cleaning. Dentures are also made of durable materials, such as acrylic polymers, that can withstand harsher cleaning conditions than teeth. As a result, dentures can be, and are, exposed to harsher cleaning conditions than teeth.

Dentures are typically cleaned in one of two ways: either the dentures are soaked for some time in a cleansing bath or dentures are brushed with dentifrices or specially formulated cleansing creams.

Brushing with creams has the advantage of supplementing the cleaning formulation with mechanical action. Unfortunately, as with teeth, spots on the dentures can be missed or overlooked during the brushing process. As a result, the denture material can degrade over time, and remaining teeth and gums of the user may be exposed to disease agents and undesirable cosmetic consequences.

Soaking in a cleansing bath offers the advantage of reaching every part of a denture for cleaning. Full immersion of the denture in the bath allows the cleansing composition to reach areas that cannot be reached by ordinary brushing with creams.

Cleansing baths are not usually sold as such. Typically, the active ingredients are sold in solid form, as a denture cleanser powder or tablet, or in concentrated liquid form. The active ingredients are then dissolved in a water bath to form the cleansing bath.

Unfortunately, soaking surrenders the advantage of mechanical scrubbing found with creams and dentifrices. To compensate for this loss of mechanical cleaning, denture cleansing tablets and powders usually contain an effervescent system and strong chemical cleaning agents.

Strong chemical cleaning agents, such as bleaches, can impart an unpleasant taste or odor to soaked dentures, however. Thus, denture cleanser manufacturers face a trade off between efficacy and cosmetic and organoleptic considerations.

Finding strong denture cleanser agents that do not impart unpleasant qualities to the dentures is an ongoing task. Acceptable agents must be nontoxic, nonstaining, and water soluble. Although not a strict requirement, the cleanser should not precipitate in the bath during cleaning to coat the denture or leave an unsightly residue in the bath.

U.S. Pat. No. 2,409,718 to Snell et al., issued Oct. 22, 1946 was an early approach to the denture cleanser agent dilemma. That patent used a water soluble salt of 2,2' dihydroxy-3,5,6,3',5',6' hexachlorodiphenylmethane as a disinfectant combined with sodium perborate as an oxidizing agent, tetrasodium pyrophosphate as a scale disintegrating material, sodium lauryl sulfo-acetate as a surface tension lowering agent, tricalcium phosphate as an anticaking agent, oil of peppermint and sodium chloride to make a denture cleanser material.

Bleaching or oxidizing materials, such as the sodium perborate in the Snell patent, have been popular ingredients in denture cleanser compositions for some time. U.S. Pat. No. 5,571,519 to Synodis et al., issued Nov. 5, 1996, teaches a two-layer tablet with a bleaching agent, such as perborate and persulfate, in combination with a flavoring agent. The separate layers prevent deterioration of the flavor by the bleaching agent on the shelf.

U.S. Pat. No. 2,498,343 to Rider et al., issued Feb. 21, 1950 (Rider I) and U.S. Pat. No. 2,498,343 to Rider et al., issued Feb. 21, 1950 (Rider II) both report oxidizing agents, such as sodium perborate and sodium percarbonate, in denture cleanser formulations. The oxidizing materials are used in combination with other ingredients, including sodium hexametaphosphate, a compound that helps with scale reduction and retards precipitation of cations in the cleansing bath.

Hexametaphosphate has also been used as an ingredient in denture cleansers.

U.S. Pat. No. 4,217,234 to Krisp et al., issued Aug. 12, 1980 (Krisp I) and U.S. Pat. No. 4,256,599 to Krisp et al., issued Mar. 17, 1981 (Krisp II) are directed to denture cleansing tablets. Krisp I is directed to a single layer tablet for "fast" cleansing of dentures, i.e., the tablet cleans dentures within about five minutes of immersion. The tablet contains sodium bicarbonate, sodium hexametaphosphate, acid disodium pyrophosphate, Caro's Acid (peroxymonosulfuric acid), amidosulfonic acid, ethylenediamine tetraacetic acid, polyethylene glycol, sodium polyacrylate, a surfactant, sodium benzoate, dialkyl thiourea and a nonionogenic fluorochemical to increase wetting. Krisp II is directed to a two-layer tablet. The tablet contains sodium bicarbonate, sodium hexametaphosphate, sulfamic acid, ethylenediamine tetraacetate (EDTA), polyethlyene glycol, a surfactant, sodium pyrophosphate, an alkali metal salt of peroxymonosulfuric acid, starch bentonite, dye, dibasic calcium phosphate and other optional ingredients.

U.S. Pat. No. 5,055,305 to Young, issued Oct. 8, 1991, is directed to a denture cleansing tablet with an inorganic persalt bleaching agent and an organic peroxyacid bleach precursor in combination with an effervescent system.

EDTA, especially in combination with oxidizing agents, has also been used in denture cleanser formulations for some time. U.S. Pat. No. 5,476,607 to Eoga et al., issued Dec. 19, 1995, (and related U.S. Pat. Nos. 5,486,304 and 5,384,062) looks to a combination of perborate and persulfate in a denture cleanser. The composition also uses enzymes and EDTA.

A similar patent, U.S. Pat. No. 5,015,408 to Reuss, issued May 14, 1991, is directed to a denture cleanser tablet with perborate, potassium monopersulphate, and an activator such as tetraacetyl ethylene diamine (TAED).

U.S. Pat. No. 4,701,223 to Eoga, issued Oct. 20, 1987, is directed to a spray-on denture cleanser having a detergent, a chelating agent, such as EDTA, and water.

U.S. Reissue Pat. No. 32,771 to Eoga, reissued Oct. 25, 1988, is directed to the combination of perborates, a fluorocarbon, and a phosphate salt. One of the sequestrants in the patent may be EDTA.

A smear layer remover is disclosed in U.S. Pat. No. 5,120,460 to Asai et al., issued Jun. 9, 1992. This patent uses a solution of EDTA in combination with a carboxyvinyl polymer, which thixotropically gels the solution, and an antibacterial agent.

Variants of EDTA have also been used. A tartar control agent comprising phosphonic acid derivatives is placed in a denture cleanser in U.S. Pat. No. 4,851,146 to Hosoi et al., issued Jul. 25, 1989. One possible derivative is ethylenediamine tetramethylphosphonic acid.

Enzymes are another material that can be used in denture cleansers. U.S. Pat. No. 4,486,330 to Yoshida et al., issued Dec. 4, 1984, uses β-1,3-glucanase to remove *Candida albicans,* a major cause of denture stomatitis, from dentures. EDTA is among the denture cleanser ingredients listed in this patent.

Denture cleansing baths are not the only potential use for a tablet, concentrate or powder cleaning material in the oral health care field, of course.

Tablets, concentrates or powders can be used with water to make mouthwashes, as in U.S. Pat. No. 3,590,121 to Schiff et al., issued Jun. 29, 1971. A chewable effervescent tablet for cleaning teeth is the subject of U.S. Pat. No. 4,753,792 to Aberg, issued Jun. 28, 1988. The tablet contains fluoride, an effervescent system, and a combination of a filling and polishing agent, such as sorbitol or mannitol, and a foam stabilizing agent such as sodium lauryl sulfate.

U.S. Pat. No. 5,437,856 to Lukacovic et al., issued Aug. 1, 1995, is directed to oral gels, toothpastes and mouthwashes containing an enzyme, a surfactant, a chelating agent and a fluoride ion source.

A water soluble effervescent tablet for use in the water bath of ultrasonic cleaning equipment is the subject of U.S. Pat. No. 5,529,788 to De Senna, issued Jun. 25, 1996. The tablet contains a proteolytic enzyme and helps ultrasonic equipment clean dental and medical instruments.

Tablets, concentrates and powders can also be used in fields other than oral health care in cleaning systems where water can be supplied independently of the cleaning agent. Cleaning systems that are not designed for oral health care, however, have very different operating constraints, and great care should be taken before adapting such cleaning systems for oral health care use.

Cleaning agents in the form of tablets, concentrates or powders are usually found outside the oral health care field as cleaners for various household uses, i.e., as laundry detergents, dishwashing detergents and hard surface cleaners. There are many formulations for carrying out various cleaning tasks. One example of such a system is found in U.S. Pat. No. 5,306,439 to Lockhart, issued Apr. 26, 1994. This patent is directed to a jewelry cleaner having tetra sodium ethylenediamine tetraacetic acid (EDTA), sodium lauryl sulfate, and an alkyl aryl sulfate in a compressed effervescent tablet.

A fabric cleaner is addressed in U.S. Pat. No. 4,299,717 to Cottrell et al., issued Nov. 10, 1981. This patent claims an alkaline detergent for fabric washing containing a detergent surfactant, an alkali metal carbonate, a pyrophosphate and phosphate builder salts.

U.S. Pat. No. 5,482,646 to Mazzola, issued Jan. 9, 1996, discusses a laundry detergent for cold water with a reduced detergent residue. The laundry detergent is claimed to contain a detergent builder (at least one-third being sodium carbonate), a granular detergent and a particulate anionic surfactant coated on the surface of the detergent granules.

Tablet or powder cleaning systems may also be used in place of traditional aqueous solution cleaners, as in U.S. Pat. No. 4,502,892 to Westermann et al., issued Mar. 5, 1985. This patent is directed to a pelleted windshield cleaner that is dissolved in water before use. The pellets contain a water soluble alkali metal polyphosphate of high molecular weight, an alkali metal carbonate or hydrogen-carbonate, a crystalline material producing an acid reaction in aqueous solution, an anionic or nonionic surfactant, and a filler, such as an alkali metal phosphate or sulfate.

A liquid laundry detergent with enzymes is the subject of U.S. Pat. No. 4,169,817 to Weber, issued Oct. 2, 1979. This patent is directed to a stabilized enzyme system that is derived from *Bacillus subtilis* and that increases the effectiveness of the detergent against proteinaceous and carbohydraceous soils. This system is reported to be stable in a composition of detergent builders, including sodium hexametaphosphate, and surfactants.

Despite the efforts in the oral health care field to develop highly effective denture cleanser systems, the search for ways to maximize the effectiveness of cleaning systems while avoiding the unpleasant consequences of strong chemical agents continues.

SUMMARY OF THE INVENTION

The principal object of the present invention therefore is to provide a cleaning material which has strong cleaning properties without the problems caused by strong chemicals, such as oxidants.

An additional object of the invention is to provide a denture cleanser tablet that provides excellent cleaning properties without the drawbacks associated with strong chemical cleaning agents.

It is an advantage of the invention that the cleaning agent of the invention does not tarnish or corrode metal surfaces often found in partial dental prostheses and orthodontic appliances.

It is another advantage of the invention that certain flavors can be used which would be unavailable in denture cleansers containing strong oxidants.

It is yet another advantage of the invention that fewer hazardous chemicals, such as strong oxidants, are required for effectiveness. This advantage is especially important for manufacturing and handling of the cleaning material.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and following the purpose of the invention, as embodied and broadly described herein, the invention provides a cleaning material containing a synergistic combination of hexametaphosphate (or a salt thereof) and ethylenediamine tetraacetic acid (EDTA) or a salt thereof in the absence of an oxidizing agent.

To further achieve the foregoing objects and by the purpose of the invention, the invention further provides a method for cleaning an object or surface comprising the steps of preparing a liquid cleaning material comprising a synergistic combination of hexametaphosphate (or a salt thereof) and ethylenediamine tetraacetic acid (EDTA) or a salt thereof in the absence of an oxidizing agent and bringing the liquid cleaning material in contact with the object, thereby cleaning the object or surface.

DESCRIPTION OF THE PREFERRED EMBODIMENTS

Reference will now be made in detail to the presently preferred embodiments of the invention.

The cleaning agent of the invention may be in any form useful for carrying out the cleaning purpose, i.e., aqueous solution, liquid concentrate, powder, tablet or other solid system. Preferably, the form is a tablet or other solid delivery system, and more preferably, the solid delivery system is an effervescent tablet or powder that is substantially water soluble.

The cleaning agent comprises an effective amount of sequestering/chelating agents to clean the desired material or surface. In the most preferred embodiment of a denture cleanser, the amount of sequestering/chelating agents in the tablet should be sufficient to cleanse dentures in a moderate volume of water, i.e., in about eight ounces of room temperature water. Cleansing does not contemplate complete and permanent removal of all contaminants from dentures, rather, the formulation should be sufficient to remove a substantial amount of plaque deposits from dentures, partial dentures, orthodontic materials and other oral health care materials formed during ordinary use. Properly applied, however, the invention provides superior plaque removal cleaning efficacy.

The sequestering/chelating agents of the invention comprise a synergistic combination of hexametaphosphate and ethylenediamine tetraacetic acid (EDTA). This synergistic combination of sequestering/chelating agents allows for a more thorough removal of plaque on dentures with conventional levels of hexametaphosphate and EDTA. Alternatively, low amounts of hexametaphosphate and EDTA may be used together to achieve levels of cleaning that would otherwise be unattainable.

The term sodium hexametaphosphate is intended to encompass a broad class of compounds having the general formula $(NaPO_3)_x$, wherein x is an integer. These salts are known as Graham's salt and may comprise a mixture of polymeric metaphosphates. The term is not limited to a specific mixture, nor is it limited to hexamers. The compounds are available commercially and are usually sold as mixtures in powders, flakes or particles. Sodium hexametaphosphate may comprise any amount by weight of a denture cleanser that forms a synergistic combination with EDTA in use. Preferably, however, sodium hexametaphosphate may comprise from about 1% by weight to about 10% by weight of a denture cleanser made in accordance with the invention, preferably from about 2% to about 10% by weight and most preferably from about 5% to about 8% by weight of the denture cleanser.

EDTA, also known as Versene Acid, edetic acid or ethylenediamine tetraacetic acid, is intended to encompass not only the acid but also salts thereof. Such salts may be full or partial salts, may be monovalent or divalent salts and may even be mixed salts. Non-limiting examples of such salts are the sodium, disodium, trisodium and calcium disodium salts of EDTA. The acid itself is preferred in the invention, but the salts thereof, especially the partial salts, and more especially the alkali partial salts of EDTA may also be used. EDTA may comprise any amount of a denture cleanser made in accordance with the invention that makes a synergistic combination with sodium hexametaphosphate. Preferably, however, EDTA comprises from about 1% by weight to about 15% by weight of the denture cleanser, more preferably from about 5% to about 12% by weight and most preferably from about 8% to about 10% by weight of the denture cleanser.

Harsh chemicals, such as bleaching or oxidizing agents, can be avoided using the synergistic combination of the invention. Thus, agents such as perborates, including anhydrous sodium perborates, sodium perborate monohydrates and monopersulfates need not be present in the formulation, especially for denture cleansers. The absence of such agents is a strong advantage of the invention, because these agents can cause tarnish or corrosion on metal surfaces, an important factor for partial denture prostheses and orthodontic materials. In addition, certain flavors, such as citrus and fruity flavors, can be adversely affected by bleaching or oxidizing agents, so conventional denture cleansers have limited flavors available. Oxidants are also strong chemicals that must be carefully handled during manufacturing and transport. The invention works well at any pH, although denture cleansers, especially effervescent tablets, usually operate in a neutral or slightly basic pH. Preferred is a range of from about 6.5 to about 8.5. Higher pH values tend to increase the cleaning effect of the combination of the invention, and there is no reason to expect that lower pH values detract meaningfully from the invention, so the invention is not limited in operation to any specific pH range.

A denture cleanser tablet in accordance with the invention may further comprise known effervescent systems, such as sodium bicarbonate and citric acid, additional sequestering/chelating agents, binders, surfactants, flavor oils, enzymes, foam stabilizing agents and lubricant systems known in the art. The formulation is preferably compressible at the high speeds necessary for commercial production, yet preferably retains its efficacy and stability. In addition, the formulation of the invention may comprise other agents known in the art for cleaning purposes including, but not limited to, enzymes.

The currently preferred embodiments of the invention are set forth in the following examples. These examples are intended to illustrate the invention and demonstrate its benefits. No limitation on the full scope and spirit of the invention is, however, to be inferred from these examples alone.

EXAMPLES 1–4

Denture cleanser tablets were prepared having the formulations set forth in Table 1. Example 1 is in accordance with the invention, while Examples 2–4 are comparative. The tablets were prepared by adding a granulation of sodium bicarbonate, sodium hexametaphosphate, polyvinyl pyrrolidone and a dye to a mixing vessel. Liquid ingredients, i.e., the fluorochemical surfactant, peppermint oil and spearmint oil, were added to the vessel, and the resulting powder blend was mixed. The remaining solid ingredients, EDTA, citric acid, sodium lauryl sulfoacetate, sodium perborate and sodium benzoate were then added to the mixing vessel, and the resulting blended powder was compressed into tablets using a Stokes tablet press with a compression force of about 8–10 tons.

Example 1 contains sodium hexametaphosphate and EDTA in synergistic amounts. Example 2 contains sodium hexametaphosphate and disodium EDTA, but not enough EDTA is present to establish a synergistic cleaning effect with the sodium hexametaphosphate. Example 3 contains EDTA but no sodium hexametaphosphate, and Example 4 contains sodium hexametaphosphate but no EDTA.

Plaque removal analyses were conducted in accordance with the t test as follows: sterilized acrylic slides were placed in Todd Hewitt broth medium with pooled human saliva and incubated overnight for plaque growth. Some slides were set aside as controls and stained using a disclosing dye solution. Reflectance readings were taken on these slides to establish controls. Other control slides were cleaned before staining. Reflectance readings were also taken on the cleaned slides as well as on unstained slides.

Slides containing plaque were then placed in a denture bath comprising a tablet from Examples 1–4 in warm water.

After 5–10 minutes, the slides were removed, and plaque was disclosed with a disclosing dye solution. The percent cleaning was calculated from reflectance readings on these slides when compared to controls using computerized statistical analysis (a "t test") that has a 95% confidence level. The results are summarized in Table 2. Plaque removal of Formula 1 was statistically significant at the 95% confidence level according to the t test when compared with the comparative examples.

The purpose of the above description is to illustrate some embodiments of the present invention without implying a limitation. It will be apparent to those skilled in the art that various modifications and variations may be made in the apparatus or procedure of the invention without departing from the scope or spirit of the invention.

TABLE 1

Formulations of Examples 1–4

| Ingredient | Weight percent | | | |
|---|---|---|---|---|
| | Ex. 1 | Ex. 2 | Ex. 3 | Ex. 4 |
| Sodium Hexametaphosphate | 6.93 | 9.02 | 0 | 4.75 |
| Versene Acid (EDTA) | 9.60 | 0 | 9.60 | 0 |
| Disodium EDTA | 0 | 0.93 | 0 | 0 |
| Sodium Bicarbonate | 39.27 | 9.15 | 46.32 | 26.90 |
| Soda Ash, Light | 10.00 | 12.90 | 10.00 | 8.10 |
| Citric Acid | 16.00 | 15.14 | 16.00 | 18.17 |
| Fluorochemical Surfactant | 0.05 | 0 | 0.05 | 0.05 |
| Proteolytic Enzyme | 1.50 | 1.61 | 1.50 | 0 |
| Peppermint Oil | 0 | 0 | 0.30 | 0.80 |
| Spearmint Oil | 0.40 | 0.40 | 0 | 0 |
| Sodium Lauryl Sulfoacetate | 4.00 | 0.93 | 4.00 | 4.00 |
| Sodium Sulfate | 0 | 11.65 | 0 | 0 |
| Potassium Monopersulfate | 0 | 22.20 | 0 | 25.00 |
| Sodium Perborate | 0 | 13.20 | 0 | 5.00 |
| Sodium Stearate | 0.50 | 0 | 0.50 | 0.50 |
| Polyethylene Glycol 8000 | 5.00 | 0 | 5.00 | 2.88 |
| Sodium Benzoate | 5.00 | 0 | 5.00 | 2.88 |
| Polyvinylpyrrolidone | 1.71 | 2.85 | 1.71 | 0.90 |
| FD&C Blue No. 2 | 0.02 | 0.01 | 0.02 | 0.03 |
| FD&C Yellow No. 5 | 0.02 | 0.01 | 0 | 0.04 |
| Total | 100.00 | 100.00 | 100.00 | 100.00 |

TABLE 2

Percent Plaque Removal, Examples 1–4

| Test | Ex. 1 | Ex. 2 | Ex. 3 | Ex. 4 |
|---|---|---|---|---|
| 1 | 82% | 19% | 20% | 69% |
| 2 | 75% | 20% | 7% | — |
| 3 | 67% | 11% | — | — |

What is claimed is:

1. A denture cleanser composition consisting essentially of:
   from about 1.0 wt % to about 10.0 wt % hexametaphosphate; and
   at least 1 wt. % EDTA,
   wherein the hexametaphosphate and EDTA provide a synergistic cleansing effect on the denture compared to a composition containing only hexametaphosphate or EDTA.

2. The cleaning composition of claim 1, wherein said alkali hexametaphosphate is sodium hexametaphosphate.

3. The cleaning composition of claim 1, wherein said EDTA is selected from the group consisting of monovalent and divalent salts of ethylenediamine tetraacetic acid.

4. The cleaning composition of claim 3, wherein said EDTA is an alkali ethylenediamine tetraacetic acid salt.

5. A denture cleanser composition consisting essentially of:
   from about 1.0 wt % to about 10.0 wt % hexametaphosphate; and
   at least 1.0 wt % to about 15.0 wt % EDTA;
   wherein the hexametaphosphate and EDTA provide a synergistic cleansing effect on the denture compared to a composition containing only hexametaphosphate or EDTA.

6. The denture cleanser composition of claim 5, wherein said hexametaphosphate is sodium hexametaphosphate.

7. The denture cleanser composition of claim 5, wherein said ethylenediamine tetraacetic acid is selected from the group consisting of monovalent and divalent salts of EDTA.

8. The denture cleanser composition of claim 7, wherein said EDTA is an alkali ethylenediamine tetraacetic acid salt.

9. A method for cleaning dentures comprising the steps of:
   preparing a cleansing composition consisting essentially of hexametaphosphate in an amount of from about 1.0 wt % to about 10.0 wt % and at least 1.0 wt % EDTA based on the total weight of the denture cleanser composition, and applying said cleansing composition to said dentures for a time sufficient to clean said dentures;
   wherein the hexametaphosphate and EDTA provide a synergistic cleansing effect on the dentures compared to a composition containing only hexametaphosphate or EDTA.

10. The method of claim 9, wherein said EDTA is present in an amount of at least 1.0 wt % to about 15.0 wt %.

11. The denture cleanser composition of claim 5 further comprising surfactants, sequestering/chelating agents, an effervescent system, binders, flavor oils, tabletting agents, enzymes, foam stabilizing agents and mixtures thereof.

12. The denture cleanser composition of claim 11 wherein said effervescent system comprises sodium bicarbonate and citric acid.

13. The denture cleanser composition of claim 11 formulated and compressed as an effervescent tablet.

14. The denture cleanser composition of claim 11 wherein said surfactant is selected from the group consisting of sodium lauryl sulfate, sodium lauryl sulfoacetate, disodium N-alkyl sulfosuccinate, disodium lauryl sulfosuccinate, sodium oleyl sulfate and mixtures thereof.

* * * * *